United States Patent [19]

Dusbabek

[11] Patent Number: 4,816,648
[45] Date of Patent: Mar. 28, 1989

[54] TOOTHBRUSH STERILIZER

[76] Inventor: Mark R. Dusbabek, 80-457 Pebble Beach, La Quinta, Calif. 92253

[21] Appl. No.: 56,811

[22] Filed: Jun. 2, 1987

[51] Int. Cl.$^4$ .............................................. H05B 3/14
[52] U.S. Cl. ................................. 219/521; 219/386; 219/505; 219/439
[58] Field of Search ............... 422/307; 219/521, 504, 219/505, 430, 438, 439, 441, 385, 386, 387, 200, 201; 312/206, 207

[56] References Cited

U.S. PATENT DOCUMENTS

| | | | |
|---|---|---|---|
| 854,257 | 5/1907 | Tobler | 219/521 |
| 1,963,557 | 6/1934 | Pain | 219/521 |
| 2,093,059 | 9/1937 | Schroder | 34/239 |
| 2,179,256 | 11/1939 | Gill | 219/218 |
| 2,180,213 | 11/1939 | Peake | 219/473 |
| 2,490,344 | 12/1949 | Fisher | 422/300 |
| 2,577,278 | 12/1951 | Sellers | 219/521 |
| 2,592,131 | 4/1952 | Farrar | 250/455.1 |
| 3,100,842 | 8/1963 | Tellefsen | 250/455.1 |
| 3,748,094 | 7/1973 | Scheidell | 312/207 |
| 3,820,251 | 6/1974 | Abernathy | 34/218 |
| 3,996,447 | 12/1976 | Douffard | 219/541 |
| 4,088,445 | 5/1978 | Ellis | 312/207 |
| 4,103,145 | 7/1978 | Oliveri | 219/222 |
| 4,307,288 | 12/1981 | Stine | 219/521 |
| 4,379,965 | 4/1983 | Dounce | 219/521 |
| 4,388,521 | 6/1983 | Thomas | 219/401 |
| 4,472,623 | 9/1984 | Futter | 219/521 |

FOREIGN PATENT DOCUMENTS 907931 3/1946 France ............... 219/521

Primary Examiner—E. A. Goldberg
Assistant Examiner—Teresa J. Walberg
Attorney, Agent, or Firm—Harvey S. Hertz

[57] ABSTRACT

A toothbrush sterilizer includes a housing member having a well formed therein for allowing the bristle portion of the toothbrush to be inserted into the interior of the well. The interior of the well defines a sterilization cavity. A closure lid is mounted on the top surface of the well, the lid having an aperture formed therein for enabling of the handle of a toothbrush to pass therethrough. Simultaneously, the lid minimizes circulation of air out of the well. A heat transfer element is juxtaposed with the exterior surface of the well. A heating element is coupled to the heat transfer element and when activated, heats the heat transfer element. The heat transfer element in turn causes the sterilization cavity to be dry heated a sufficient amount to sterilize the toothbrush bristles of the toothbrush positioned within the sterilization cavity.

2 Claims, 1 Drawing Sheet

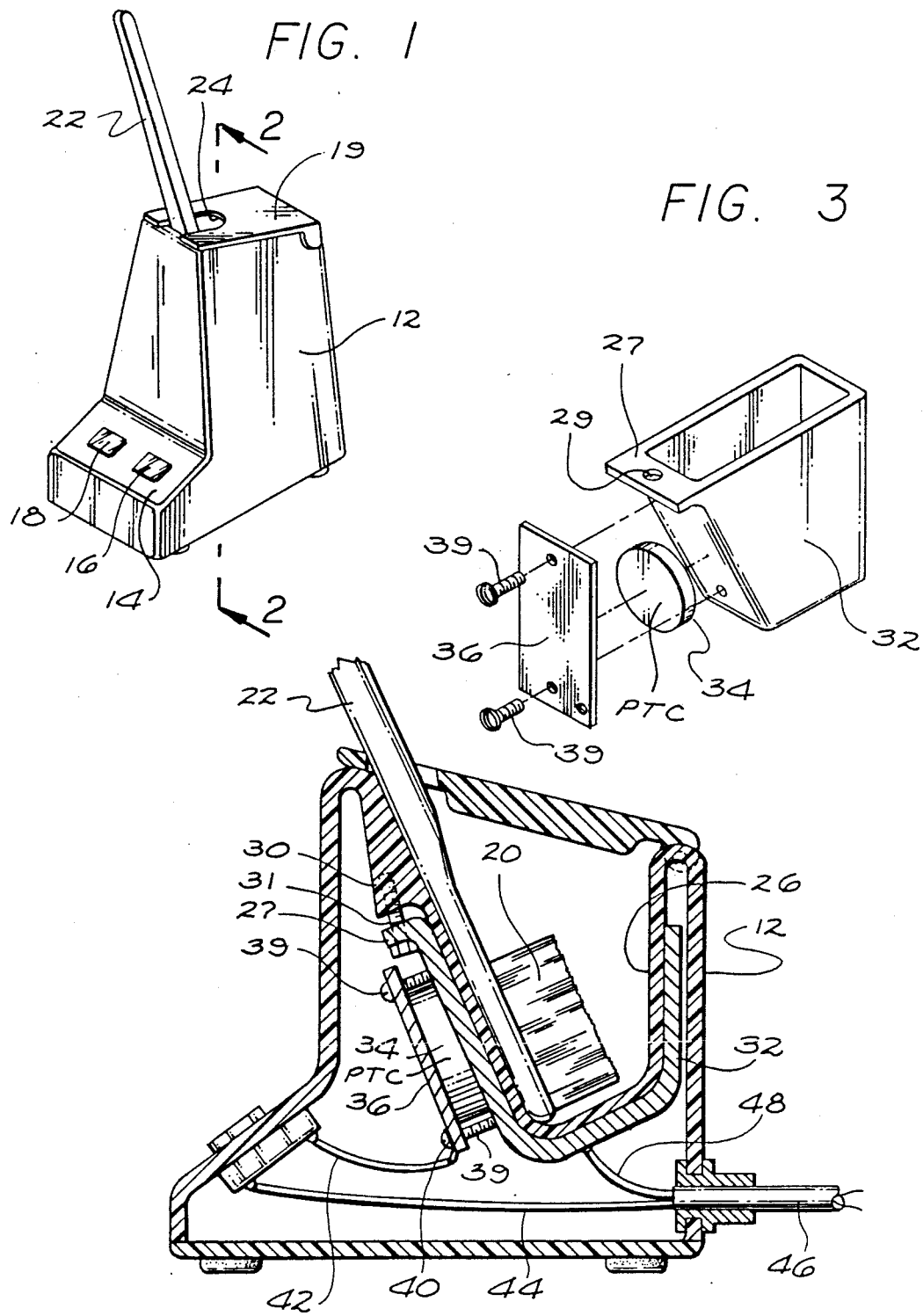

TOOTHBRUSH STERILIZER

BACKGROUND OF THE INVENTION

1. Field of The Invention

The field of art to which the invention pertains includes the field of toothbrush sterilizers and, more particularly, to a dry heat sterilization chamber for toothbrush bristles.

2. Description of The Prior Art

Recent medical studies indicate that lingering sore throats and other bacterial infections can be traceable to bacteria found on toothbrushes. Additional studies further indicate that viral infections may be transmitted via toothbrushes as well. Moreover, it has been found that even new toothbrushes have been found to be contaminated with bacteria so that frequent replacement of a toothbrush may not be the obvious solution to solving this problem.

Toothbrush sterilizers are known. Typically, the conventional toothbrush sterilizer uses ultra-violet lamps to illuminate a large cavity where multiple toothbrushes can be inserted. Known toothbrush sterilizers include U.S. Pats. Nos. 2,180,213; 2,592,131; 3,100,842; 3,748,094; and 4,088,445. Other drying and heating cabinets which could be used for sterilization include U.S. Pats. Nos. 2,093,059; 2,179,256 and 2,490,344. U.S. Pat. No. 4,103,145 illustrates a heating chamber which could be used as an oven for a curling iron.

Other known prior art include U.S. Pats. Nos. 4,472,623 and 4,379,965 which relate to disinfecting chambers for contact lenses.

The present invention provides a heating chamber providing a source of dry heat for sterilizing a single toothbrush. When the dry heat is transferred to the toothbrush bristles for a sufficient period of time, it has been found that the toothbrush bristles will be effectiveoly disinfected as the dry heat provides a sufficient sterilization agent for the wet toothbrush.

The advantages of this invention, both as to its construction and mode of operation, would be readily appreciated as the same becomes better understood by reference to the following detailed description when considered in connection with the accompanying drawings in which like reference numerals designate like parts throughout the figures.

BRIEF DESCRIPTION OF THE DRAWINGS

FIG. 1 is a perspective view of the toothbrush sterilizer;

FIG. 2 is a cross-sectional view of the toothbrush sterilizer of FIG. 1 taken along the line to 2—2 thereof; and FIG. 3 is an exploded perspective view of the heat transfer element used in the toothbrush sterilizer.

DESCRIPTION OF THE PREFERRED EMBODIMENT

Referring now to the drawings, there shown in FIG. 1. a toothbrush sterilizer constructed in accordance with principles of the invention. The sterilizer includes a housing 12 of generally a trapezoidal shaped configuration having a front angled plate 14 containing a power indicator light 16 and a conventional on/off switch 18 for operating the toothbrush sterilizer. A hinged lid 19 provides access to the interior of the housing 12, into which the bristle portion (not shown in FIG. 1) of a toothbrush which is to be sterilized is inserted. The handle portion of the toothbrush 22 extends through an aperture 24 formed in the hinged lid 19.

The sterilizer is shown in greater detail in FIG. 2 and 3 and includes a sterilization cavity 26 into which the bristle portion 20 of the toothbrush 22 is inserted. The sterilization cavity 26 and the housing 12 typically could be made of one piece moulded plastic having sufficient qualities to resist the temperatures present found in the present invention. The sterlization cavity 26 as illustrated in FIG. 2 is formed from the continuous walls of the top edge of the housing 12.

Surrounding the sterilization cavity 26 and juxtaposed with its outer surface is a heat transfer well 32. The heat transfer well 32 is illustrated as having a generally truncated configuration having an enlarged open top end which is positioned on to the exterior surface of the sterilization cavity from the lower end from the bottom of the housing 12.

A flange 27 forms an extension of the top surface of the heat transfer well 32. The flange 27 contains an aperture 29 which is aligned with an opening of an enlarged lip 30 of the wall of cavity 26. A screw 31 passing through the aperture 29 is used to fasten the heat transfer well 32 to the cavity 26 at the lip 30.

The interior dimensions of the heat transfer well 32 are equal to the exterior dimensions of the sterilization cavity so that heat generated from a heating element 34 positioned adjacent the exterior surface of the heat transfer well 32 will be transferred very efficiently to the interior of the sterilization cavity 26.

The heating element 34 could be of the type described in U.S. Pat. No. 3,996,447 which is a disc-like ceramic resistor element of a material of positive temperature coefficient of resistivity. The heating element 34 is secured adjacent the exterior surface of the heat transfer well 32 by means of a retaining plate 36 fastened to the well by non-conductive screws 39, typically made of insulating material.

An electrical lug 40 is secured to the retaining plate 36 to and forms an electrical connection via lead 42 to the on/off switch 18. Another lead 44 is connected between the on/off switch 18 and the input AC power line 46 connected to the housing. The input lead 48 from the housing line is connected to the heat transfer well 32. Thus, when the power switch 18 is activated, electrical current will flow through the heat transfer well 32, the heating element 34, the electrical conductor 42, the power switch 18 and hence back to the AC power line 46 via the electrical conductor 44.

It has been found that the heating element 34 generates sufficient heat which is transferred to the well 32 so that if the temperature of the sterilization cavity 26 which is 200 degrees Farenheit for approximately one hour, the toothbrush bristles 28 of the toothbrush subjected to this dry heat would be sterilized. Typically, a conventional timer (not shown) would normally be built into the on/off power switch 18 to automatically activate the power for the desired amount of time.

The lid 19 is utilized to enclose the sterilization cavity 26 so that air circulation out of the sterilization cavity 26 is minimized. The lid 19 is of enlarged thickness as compared to the rest of the outer wall of housing 12 as it is used as an insulating cover for the sterilization cavity 26. Further, the width of the sterilization cavity 26 is normally designed so that it is slightly greater than the width of a conventional toothbrush yet wide enough to enable the cavity to be cleaned when necessary.

The housing 12, the hinged lid 19 and the sterilization cavity could all be molded from Thermalux polysulfone manufactured by Westlake Plastic Company of Lenni, Pennsylvania. This material is specifically designed for medical applications which is subjected to repeated dry heat sterilization temperatures and is a tough, rigid, high strength thermoplastic which maintains its properties over a wide range of temperatures to above 300 degrees Farenheit.

I claim:

1. A toothbrush sterilizer comprising: a housing member having a sterilization cavity formed therein for allowing a bristle portion of a toothbrush to be inserted into an interior of said cavity, said interior of said caivty defining said sterilization cavity, said sterilization cavity having four side walls and an interconnecting bottom wall;

a closure lid mounted on a top surface of said cavity, said lid having an aperture formed therein for enabling a handle of a toothbrush to pass therethrough and simultaneously minimizing air cirulation of air out of said cavity;

a heat transfer element defining a well surrounding the exterior surface of said cavity at an outer surface of said cavity bottom wall and at least a portion of said cavity side walls; and a heating element coupled to said heat transfer element, said heating element when activated heating said heat transfer element, said heat transfer element in turn causing said sterilization cavity to be heated a sufficient amount to sterilize bristles of a toothbrush positioned in said sterilization cavity.

2. A toothbrush sterilizer in accordance with claim 1 wherein said cavity width is slightly greater than the width of a toothbrush in at least one dimension.

* * * * *